United States Patent [19]

Miller et al.

[11] Patent Number: 5,581,853
[45] Date of Patent: Dec. 10, 1996

[54] DEVICE FOR RESTRAINING PRISONERS IN THE COMPARTMENT OF AN AUTOMOBILE

[76] Inventors: J. Daniel Miller, 13615 173rd Pl. N.E., Redmond, Wash. 98052; Mitch Y. Choi, 7939 8th Ave. S.W., Seattle, Wash. 98106

[21] Appl. No.: 273,508

[22] Filed: Jul. 11, 1994

[51] Int. Cl.$^6$ ........................................ A61F 5/37
[52] U.S. Cl. .................... 24/302; 70/16; 297/466
[58] Field of Search ................ 70/16, 17; 119/769–771; 297/468, 466; 280/801.1, 290; 128/876, 882; 24/298–302

[56] References Cited

U.S. PATENT DOCUMENTS

| | | |
|---|---|---|
| 2,665,143 | 1/1954 | Rusmussen. |
| 4,004,583 | 1/1977 | Johnson ................................. 297/468 |
| 4,292,932 | 10/1981 | Wooderson .............................. 119/771 |
| 4,422,455 | 12/1983 | Olsen .................................. 128/882 X |
| 4,784,889 | 11/1988 | Daniels. |
| 4,788,941 | 12/1988 | Villeneuve .......................... 128/876 X |

*Primary Examiner*—James R. Brittain
*Attorney, Agent, or Firm*—Harry M. Cross, Jr.

[57] ABSTRACT

A prisoner restraint device that permits a prisoner's lower legs or wrists to be secured in an adjustable loop at one end of a restraint strap and restrained close to one of the vehicle's doors comprises (a) a restraint buckle at one end of the strap so that the strap can be placed around a prisoner's lower legs or wrists and fastened into an adjustable loop, and (b) a moveable locking clip at the other end of the strap so that the strap can be extended through a closed vehicle door and the moveable locking clip wedged against the outside of the vehicle to secure the prisoner's bound limbs when the strap is pulled taut.

5 Claims, 3 Drawing Sheets

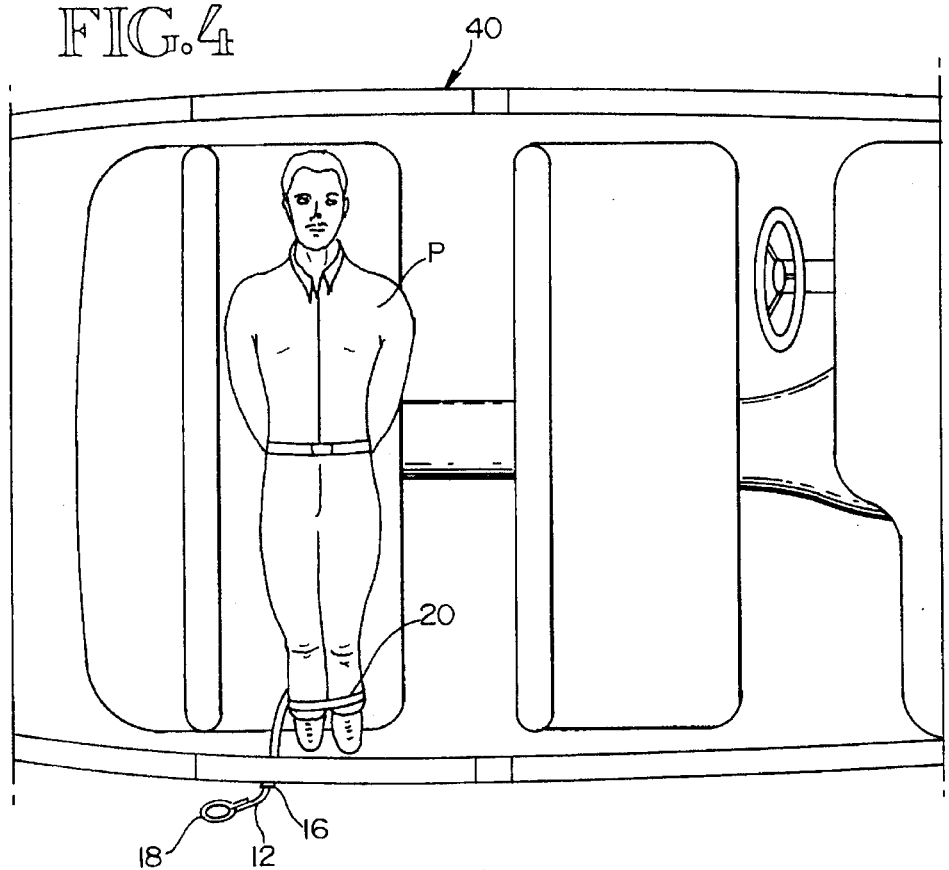
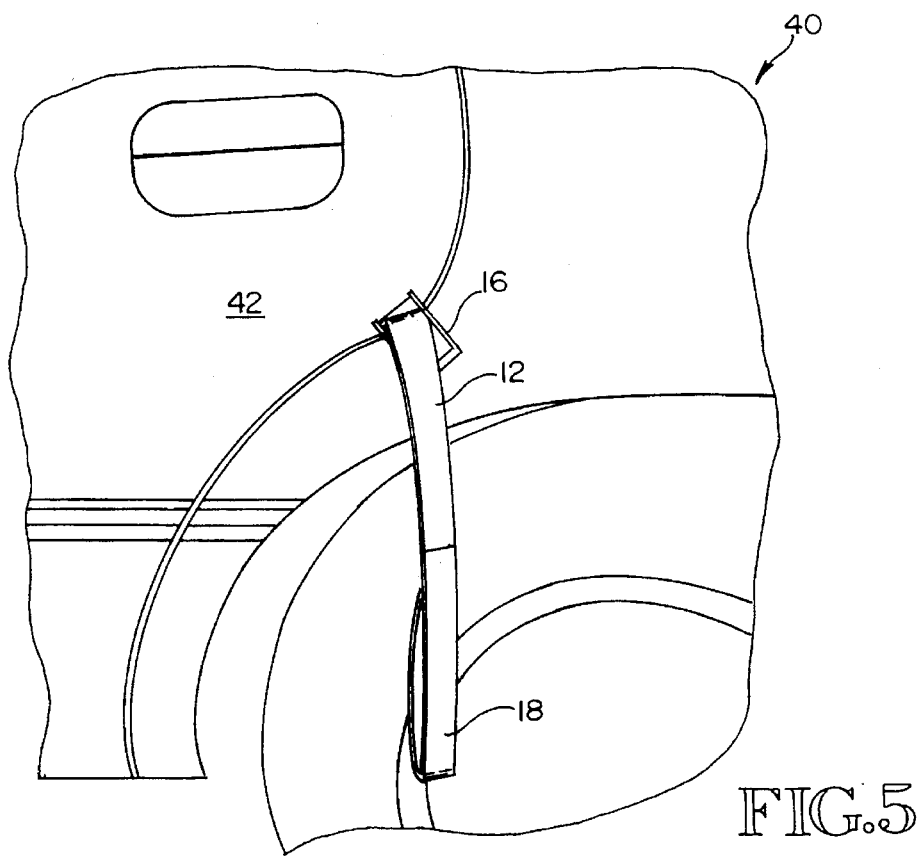

5,581,853

1

DEVICE FOR RESTRAINING PRISONERS IN THE COMPARTMENT OF AN AUTOMOBILE

FIELD OF THE INVENTION

This invention relates to restraints straps employed by law enforcement officials to restrain prisoners; and more particularly to leg restraints used to restrain prisoners in a patrol car.

BACKGROUND OF THE INVENTION

When prisoners are transported by law enforcement officials, two primary concerns exist. One is the protection of the law enforcement officers and equipment, such as automobiles. The other is the restraint of the prisoner without undue harm to his body. Unruly prisoners are especially difficult to hands safely.

When prisoners are transported by police car, they are usually handcuffed and placed in the rear seat compartment. Even though handcuffed, unruly prisoners have a considerable ability to move around. They can position themselves so as to slam their feet against doors and windows, often causing damage to the car's interior. Particularly physical prisoners have been known to break out windows, for example. When such prisoners exhibit such extreme behavior, they also pose a danger to the police officer.

SUMMARY OF THE INVENTION

The present invention comprises an elongated prisoner restraint device that permits a prisoner's lower legs or wrists to be secured in an adjustable loop at one end of a restraint strap and restrained close to a doorway. The restraint strap is extended through an open doorway, after the prisoner is placed with his bound limbs adjacent the doorway, and the door is closed on the strap. The portion of the strap external to the door is then pulled to force the prisoner's bound limbs into close proximity with the closed door. The restraint strap is provided (a) with latching means at one end of the strap so that the strap can be placed around a prisoners lower legs or wrists and buckled into an adjustable loop, and (b) with a moveable locking clip at the other end of the strap so that any slack in the strap can be taken up, when extended through a closed door, by moving the locking clip toward the closed door and wedging it against the outside of the door to secure the prisoner's bound limbs when the strap is pulled taut. The invention is suited especially for use to restrict a prisoner placed in the rear sear of a patrol vehicle. The invention may also be used to restrict a prisoner placed in a holding cell.

In particular, the present invention comprises an elongated prisoner restraint device that permits a prisoner's lower legs or wrists to be secured in an adjustable loop at one end of a restraint strap and restrained closed to one of the vehicle's doors. The restraint strap is extended through an open doorway of the vehicle, after the prisoner is placed in a vehicle with his bound limbs adjacent the doorway of the vehicle, and the door is closed on the strap. The portion of the strap external to the vehicle is then pulled to force the prisoner's bound limbs into close proximity with the close door. The restraint strap is provided (a) with latching means at one end of the strap so that the strap can be placed around a prisoner's lower legs or wrists and fastened into an adjustable loop, and (b) with a moveable locking clip at the other end of the strap so that the strap can be extended through a closed vehicle door and the moveable locking clip wedged against the outside of the vehicle to secure the prisoner's bound limbs when the strap is pulled taut.

The restraint device of this invention comprises an elongated restraint strap having a restraint end and a control end, restraint buckle means having a first section fastened to the restraint end of said strap and a second section slidably carried by said strap, control handle means fastened to the control end of said strap, and releasable locking clip means slidably carried by said strap between the second section of said restraint buckle means and said control handle means. The first and second sections of the restraint buckle means forms an adjustable restraint loop when the first and second sections are fastened together. The locking clip means is slidable along the restraint strap in a direction toward the restraint loop, and is only slidable in an opposite direction when released whereby the strap can be buckled around a person with the restraint loop encircling a portion of the person's body and drawn taut therearound, The person then can be positioned on one side of a closed door and held thereagainst by the strap being extended through a doorway closed by the closed door with the locking clip means bearing against the other side of the closed door to maintain the strap in a taut condition.

A method of restraining a prisoner according to this invention comprises the steps of providing a restraint device according to preceding paragraph, encircling the restraint strap of the restraint device around the limbs of the prisoner and buckling the restraint buckle means so as to cause the prisoner's limbs to be encircled by the restraint loop of said restraint device, placing the prisoner on one side of a doorway having a swinging door associated therewith, extending the restraint strap through the doorway so that the locking clip means is on the opposite side of the doorway from the prisoner and closing the door on the restraint strap, and sliding the locking clip means against the closed door, thereby drawing the restraint strap taut with the restraint loop closely encircling the prisoner's limbs whereby the prisoner is restrained against the closed door.

BRIEF DESCRIPTION OF THE DRAWINGS

FIG. 4 is a plan view of the inside of a patrol car, showing a prisoner with his lower legs restrained by the restraint strap and showing the restraint strap extending through the closed doorway of the vehicle that is adjacent the prisoner's bound legs;

FIG. 5 is a partial side view in elevation of a patrol car showing the restraint strap extending through the closed doorway and showing the cam buckle positioned against the edge of the closed door to maintain the prisoner's legs in the position shown in FIG. 4.

DETAILED DESCRIPTION OF THE INVENTION

Figure 1:
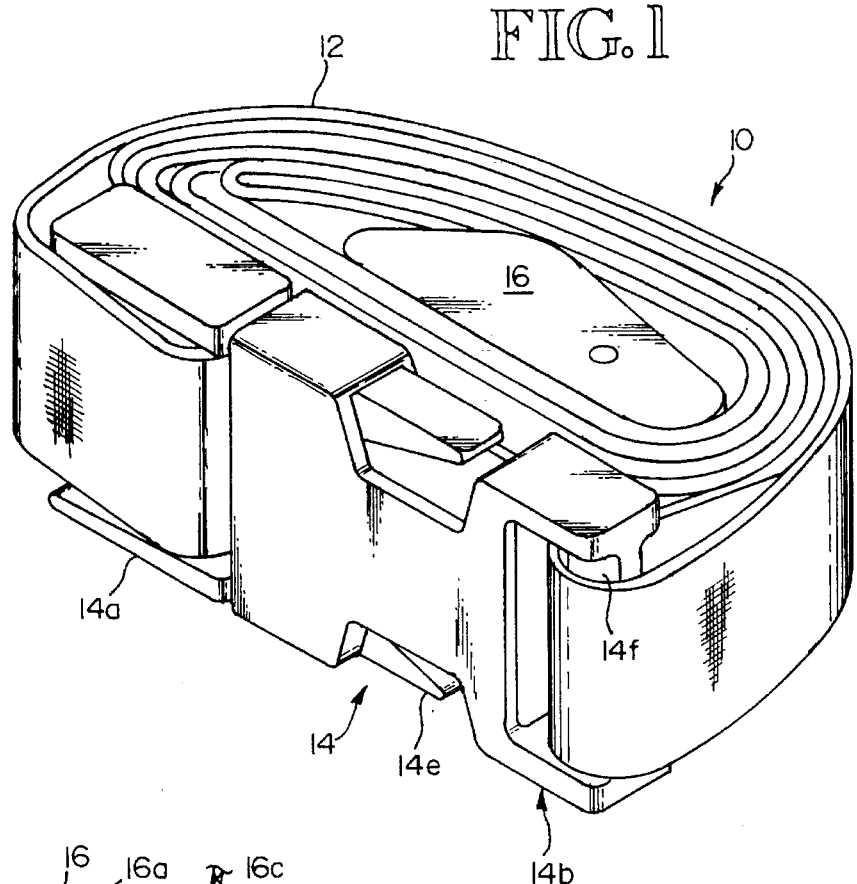
FIG. 1 is a view in perspective of the elongated restraint strap of this invention folded or wrapped into a compact package for storage.

The restraint device 10 of this invention comprises a restraint strap 12, a side-release buckle 14 and a cam buckle locking clip 16. The side-release buckle 14 comprises a male section 14a and a female section 14b. The buckle female section 14b is secured to one end of the restraint strap 12; the restraint strap 12 being extended through the female section 14b, doubled back on itself, and fastened to itself by stitching. At the other end of the restraint strap 12, a control handle 18 is provided by doubling the strap back on itself, and fastening the overlapped end itself by stitching to provide a hand loop. the male section 14a of buckle 14 slides freely on the strap 12 so that it can be latched to the female section 14b to provide a restraint loop 20. Because male section 14 a slides freely on strap 12, the loop 20 is freely adjustable. Consequently, the restraint end of strap 12 (the end to which the female section 14b of buckle 14 is secured) can be wrapped around an object and the two buckle sections, 14a, 14b, secured together, and then the thus-formed restraint loop 20 can be drawn taut about the object by pulling on the control handle 18.

Each latching buckle section, 14a, 14b, is comprised of a latching portion and a strap mounting section. Male section 14a is a one piece, plastic member having flexible latching prongs 14c and a cross-channel 14d through which the restraint strap 12 passes. Female section 14b is a one piece, plastic member having a latching compartment 14e for receiving the latching prongs 14c and a cross bar 14f around which the restraint strap 12 passes.

Figure 2:
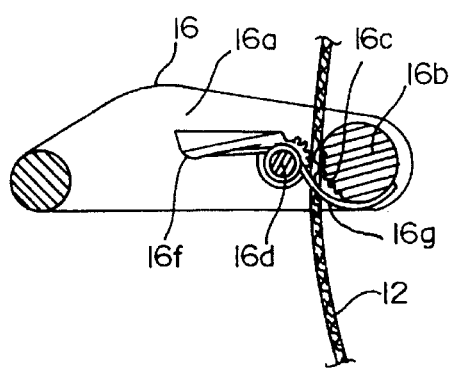
FIG. 2 is a view in cross-section of a cam buckle locking clip, showing the restraint strap extending through the buckle.
Figure 3:
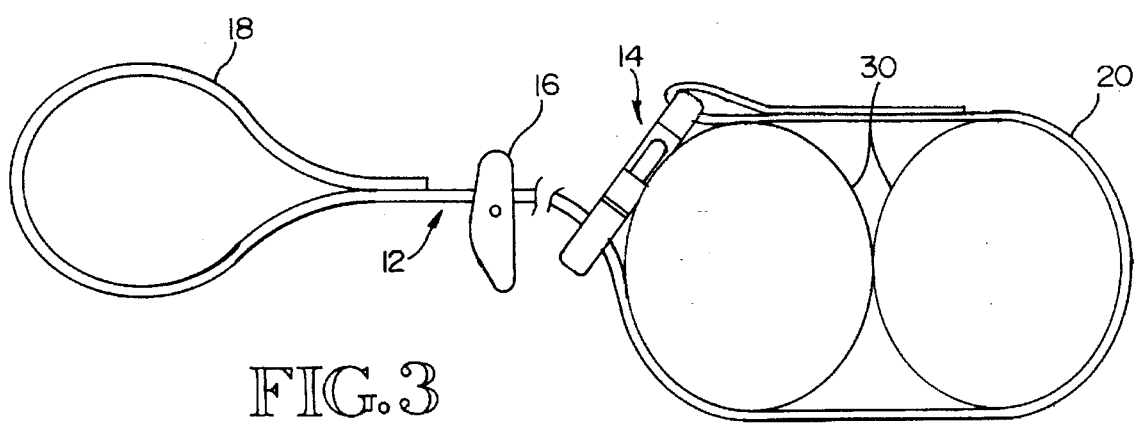
FIG. 3 is a plan view of the elongated restraint strap of this invention showing it buckled around a prisoner's legs or wrists at one end and showing the cam buckle locking clip positioned at the other end of the strap.
Figure 6:
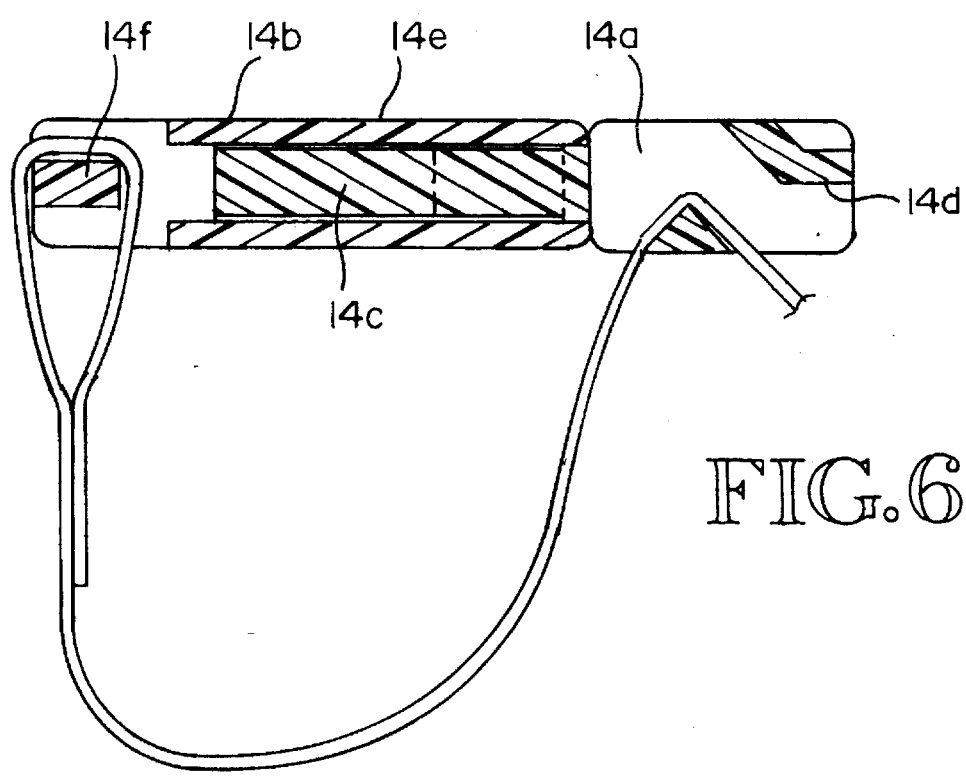
FIG. 6 is a view in cross-section of the restraint strap with one end attached to one section of a side-release latching buckle and with the restraint strap slidably extended through the other section of the latching buckle.

The cam buckle locking clip 16 comprises a metal housing 16a through which the restraint strap 112 passes, a cross shaft 16b that has a longitudinally-ribbed surface portion 16c facing inward, and a spring-loaded release 16d that has a toothed surface 16e facing the ribbed surface 16c. Release 16d includes a release lever 16f and a coil spring 16g that rotatably biases the toothed surface 16e toward the ribbed surface 16c. The restraint strap 12 passes through housing 16a between cross shaft 16b and release 16d as shown in FIG. 2. Cam buckle locking clip 16 is oriented on strap 12 such that it can be pushed along strap 12 toward the restraint end, and such that it cannot be pushed along the strap 12 toward the control handle end without pressing on release lever 16f to rotate release 16d out of binding engagement with strap 12. When strap 12 is attempted to be pulled through the cam buckle locking clip 16 from the restraint end, the strap 12 will be pinched between the ribber surface 16g and the toothed surface 16e and prevented from slipping through.

When the restraint device of this invention is used to restrain a prisoner's legs against kicking in a patrol car, the following procedure would be followed. First the side release buckle sections would be separated and the restraint end of the strap 12 would be encircled around the prisoner's ankles 30. Then the side release buckle sections would be fastened together and the loop 20 thus formed would be tightened around the ankles by pulling on the control handle end of the strap 12. The prisoner P would be placed on the rear seat of a patrol car 40 with his feet toward the doorway. The cam buckle locking clip 16 would then be pushed up against the control handle 18 if it had not already been located there. The strap 12 would then be extended past the door frame of the car and the car door 42 would be closed on the strap 12. The strap 12 would be pulled taut so that the buckled restraint loop 29 would be snug around the prisoner's ankles and then the cam buckle locking clip 16 would be pushed firmly against the closed car door 42. The control handle would then be released and the portion of the strap hanging outside of the car would hang freely as shown in FIG. 5. For use in conjunction with a patrol car, the length of strap 12 is selected so that the outside end of the strap will not hang to the ground or become entangled with the car's tire. The strap length is long enough, however, that an officer will have control over the prisoner's ankles from a distance.

Since the cam buckle locking clip can only be freely pushed toward the car door, once it is secured against the car's side, the prisoner's feet on the other side of the door are secured against the car door. The locking clip will maintain the strap 12 taut. This prevents the prisoner from kicking out the car windows and otherwise limits his mobility. To release the prisoner, the cam buckle locking clip release lever 16f is pressed to rotated the toothed surface 16e away from the ribbed surface 16c, thereby freeing the strap 12. The locking clip 16, when release lever 16f is pressed, can be easily slid along strap 12 toward the control handle 18. Then the car door 42 can be opened and the prisoner taken out.

A substantially similar procedure may be employed to restrain a prisoner in a holding cell. When the restraint strap is placed around the prisoner's ankles and the prisoner is placed on the cell floor with his feet toward the doorway, the cell door can be closed on the strap, the strap pulled taut, and the locking clip slid up against the outside of the door.

A prisoner's wrists may be secured in the same manner. For some particularly unruly prisoners, it may be desirable to secure their ankles with their feet adjacent one car door and to secure their wrists with their hands adjacent to opposite car door, using two restraint devices in the process.

The restraint strap preferably comprises a 52 inch long, 1 inch wide polypropylene strap stitched to provide the loop handle at one end. At the other end of the strap, the female half of the side release buckle is sewn in. The strap is inserted through the male half of the side release buckle so that the male half may slide up and down the strap. Between the male half of the buckle and the loop end of the strap, the strap is inserted through the slidable cam buckle. The side release buckle and the cam buckle could be an ANCRA 1 inch cam buckle, part # 41030-10.

While the preferred embodiment of the invention has been described herein, variations in the design may be made. The scope of the invention, therefore, is only to be limited by the claims appended hereto.

The embodiments of the invention in which an exclusive property is claimed are defined as follows:

What is claimed is:

1. A restraint device comprising an elongated restraint strap having a restraint end and a control end; restraint buckle means having a first section fastened to the restraint end of said strap and a second section slidably carried by said strap; control handle means fastened to the control end of said strap; and releasable locking clip means slidably carried by said strap between the second section of said restraint buckle means and said control handle means; said first and second sections of said restraint buckle means forming an adjustable restraint loop when the first and second sections are fastened together; said locking clip means being manually slidable along said restraint strap in a direction toward the restraint loop, and only slidable in an opposite direction when released whereby said strap can be buckled around a person with the restraint loop encircling a portion of the person's body and drawn taut therearound, and the person can be positioned on one side of a closed door and held thereagainst by said strap being extended through a doorway closed by the closed door with said locking clip means bearing against the other side of the closed door to maintain the strap in a taut condition; and said locking clip means comprising a cam buckle through which said strap extends, said cam buckle having releasable binding means normally in binding engagement with said strap and constructed and arranged whereby said cam buckle can be freely moved toward said restraint loop but can be moved in an opposite direction only when said binding means is released from binding engagement with said strap.

2. The restraint device of claim 1 wherein said restraint strap is doubled back on itself and fastened to itself so as to form said control handle means.

3. The restraint device of claim 1 wherein said restraint buckle means comprises a side release buckle having male and female portions with said male portion providing one of the first and second sections of the restraint buckle means, and with said female portion providing the other of the first and second sections of the restraint buckle means.

4. A method of restraining a prisoner comprising the steps of providing a restraint device according to claim 1; encircling the restraint strap of said restraint device around the limbs of the prisoner and buckling the restraint buckle means so as to cause the prisoner's limbs to be encircled by the restraint loop of the restraint device; placing the prisoner on one side of a doorway having a swinging door associated therewith; extending the restraint strap through the doorway so that the locking clip means is on the opposite side of the doorway from the prisoner and closing the door on the restraint strap; sliding the locking clip means against the closed door, thereby drawing the restraint strap taut with the restraint loop closely encircling the prisoner's limbs whereby the prisoner is restrained against the closed door.

5. A restraint device comprising an elongated restraint strap having a restraint end and a control end; restraint buckle means having a first section fastened to the restraint end of said strap and a second section slidably carried by said strap; control handle means fastened to the control end of said strap; and releasable locking clip means slidably carried by said strap between the second section of said restraint buckle means and said control handle means; said first and second sections of said restraint buckle means forming an adjustable restraint loop when the first and second sections are fastened together; said locking clip means being manually slidable along said restraint strap in a direction toward the restraint loop, and only slidable in an opposite direction when released whereby said strap can be buckled around a person with the restraint loop encircling a portion of the person's body and drawn taut therearound, and the person can be positioned on one side of a closed door and held thereagainst by said strap being extended through a doorway closed by the closed door with said locking clip means bearing against the other side of the closed door to maintain the strap in a taut condition; said locking clip means comprising a cam buckle through which said strap extends, said cam buckle having releasable binding means normally in binding engagement with said strap and constructed and arranged whereby said cam buckle can be freely moved toward said restraint loop but can be moved in an opposite direction only when said binding means is released from binding engagement with said strap; said restraint strap being doubled back on itself and fastened to itself so as to form said control handle means; and said restraint buckle means comprising a side release buckle having male and female portions with said male portion providing one of the first and second sections of the restraint buckle means, and with said female portion providing the other of the first and second sections of the restraint buckle means.

* * * * *